(12) United States Patent
    Wang

(10) Patent No.: US 12,397,115 B2
(45) Date of Patent: Aug. 26, 2025

(54) INJECTION DEVICE

(71) Applicant: Jabil Circuit (Shanghai) Co., Ltd., Shanghai (CN)

(72) Inventor: De Yu Wang, Shanghai (CN)

(73) Assignee: Jabil Circuit (Shanghai) Co., Ltd., Shanghai (CN)

( * ) Notice: Subject to any disclaimer, the term of this patent is extended or adjusted under 35 U.S.C. 154(b) by 847 days.

(21) Appl. No.: 17/685,485

(22) Filed: Mar. 3, 2022

(65) Prior Publication Data

US 2022/0280724 A1    Sep. 8, 2022

(30) Foreign Application Priority Data

Mar. 8, 2021 (CN) .......................... 202110250319.X

(51) Int. Cl.
    *A61M 5/20*     (2006.01)
    *A61M 5/178*    (2006.01)
    *A61M 5/24*     (2006.01)
    *A61M 5/31*     (2006.01)
    *A61M 5/315*    (2006.01)

(52) U.S. Cl.
    CPC .............. *A61M 5/20* (2013.01); *A61M 5/178* (2013.01); *A61M 5/24* (2013.01); *A61M 5/31* (2013.01); *A61M 5/315* (2013.01); *A61M 5/31546* (2013.01); *A61M 2005/2006* (2013.01); *A61M 2205/14* (2013.01); *A61M 2205/3317* (2013.01); *A61M 2205/3379* (2013.01); *A61M 2205/8212* (2013.01)

(58) Field of Classification Search
    CPC .......... A61M 5/20; A61M 5/178; A61M 5/24; A61M 5/31; A61M 5/315; A61M 5/31546; A61M 2005/2006; A61M 2205/14; A61M 2205/3317; A61M 2205/3379; A61M 2205/8212
    See application file for complete search history.

(56) References Cited

U.S. PATENT DOCUMENTS

| 2016/0120751 | A1  | 5/2016  | Mounce et al. |
| 2018/0353699 | A1* | 12/2018 | Helmer ................... A61M 5/20 |
| 2019/0143051 | A1  | 5/2019  | Srinivasan et al. |
| 2020/0093993 | A1  | 3/2020  | O'Rourke et al. |

FOREIGN PATENT DOCUMENTS

| JP | 2013148473 A  | 8/2013 |
| WO | 2020115031 A1 | 6/2020 |

OTHER PUBLICATIONS

Search Report issued to European counterpart application No. 22160514.0 by the EPO on Jul. 27, 2022.

* cited by examiner

*Primary Examiner* — Tasnim Mehjabin Ahmed
(74) *Attorney, Agent, or Firm* — Young Basile Hanlon & MacFarlane, P.C.

(57) ABSTRACT

An injection device includes a case body, a control circuit disposed on the outside of the case body, a movable part disposed in the case body, carrying a drug, and movable between a start position and a target position, a magnetic member movable along with the movable part and producing a magnetic field, and a magnetic switch disposed on the outside of the case body and connected to the control circuit. When the movable part is moved to the target position, the magnetic switch changes a status of a conductive path of the magnetic switch in response to a presence of the magnetic field. The control circuit changes a state of the injection device according to a change of the status of the conductive path.

18 Claims, 4 Drawing Sheets

INJECTION DEVICE

CROSS-REFERENCE TO RELATED APPLICATION

This application claims priority to Chinese Invention Patent Application No. 202110250319.X, filed on Mar. 8, 2021.

TECHNICAL FIELD

The disclosure relates to an injection device, and more particularly to an injection device capable of changing its state when being operated.

BACKGROUND

An injection device is used to administrate a drug or a medicine into a body of a human or an animal for treatment or wellness promotion. With the development of society and technology, mechanical injection devices no longer satisfy the current needs, and injection devices evolve toward being smart, multifunctional and automated. For example, a detection function is added to an injection device to determine whether a drug to be injected is properly filled in the injection device. However, a conventional injection device with the detection function is still flawed in some ways, such as having a complicated structure and poor reliability.

SUMMARY

Therefore, an object of the disclosure is to provide an injection device that can alleviate at least one of the drawbacks of the prior art.

According to a first aspect of this disclosure, an injection device includes a device case body that has an accommodating space, a control circuit that is disposed on the outside of the device case body, a movable part that is disposed in the accommodating space of the device case body, that carries a drug for injection, and that is movable relative to the device case body between a start position and a target position, a magnetic member that is disposed on the movable part, that is movable along with the movable part, and that produces a magnetic field, and a magnetic switch that is disposed on the outside of the device case body, that is disposed proximate to the magnetic member when the movable part is at the target position, and that is electrically connected to the control circuit. When the movable part is moved to the target position, the magnetic switch changes a status of a conductive path of the magnetic switch in response to presence of the magnetic field that is produced by the magnetic member disposed on the movable part. The control circuit changes a state of the injection device according to a change of the status of the conductive path of the magnetic switch.

According to a second aspect of this disclosure, an injection device includes a device case body that has an accommodating space, a control circuit that is disposed on the outside of the device case body, a movable part that is disposed in the accommodating space of the device case body, and that is movable along a longitudinal direction of the device case body between a start position and a target position, a magnetic member that is disposed on the movable part, that is movable along with the movable part, and that produces a magnetic field, a magnetic switch that is disposed on the outside of the device case body, that is disposed proximate to the magnetic member when the movable part is moved to the target position, and that is electrically connected to the control circuit. The device case body isolates the control circuit and the magnetic switch from the accommodating space of the device case body. When the movable part is moved to the target position, the magnetic switch changes a status of a conductive path of the magnetic switch in response to presence of the magnetic field that is produced by the magnetic member disposed on the movable part. The control circuit changes a state of the injection device according to a change of the status of the conductive path of the magnetic switch.

According to a third aspect of this disclosure, an injection device includes a device case body that has an accommodating space, a control circuit that is disposed on the outside of the device case body, a movable part that is disposed in the accommodating space of the device case body, and that is movable along a longitudinal direction of the device case body between a start position and a target position, a magnetic member that is disposed on the movable part, that is movable along with the movable part, and that produces a magnetic field, a magnetic switch that is disposed on the outside of the device case body, that is disposed proximate to the magnetic member when the movable part is moved to the target position, and that is electrically connected to the control circuit. The device case body isolates the control circuit and the magnetic switch from the accommodating space of the device case body. When the movable part is moved to the target position, the magnetic switch changes a status of a conductive path of the magnetic switch in response to presence of the magnetic field that is produced by the magnetic member disposed on the movable part to pass a signal to the control circuit. The control circuit changes a state of the injection device according to the signal passed by the magnetic switch.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
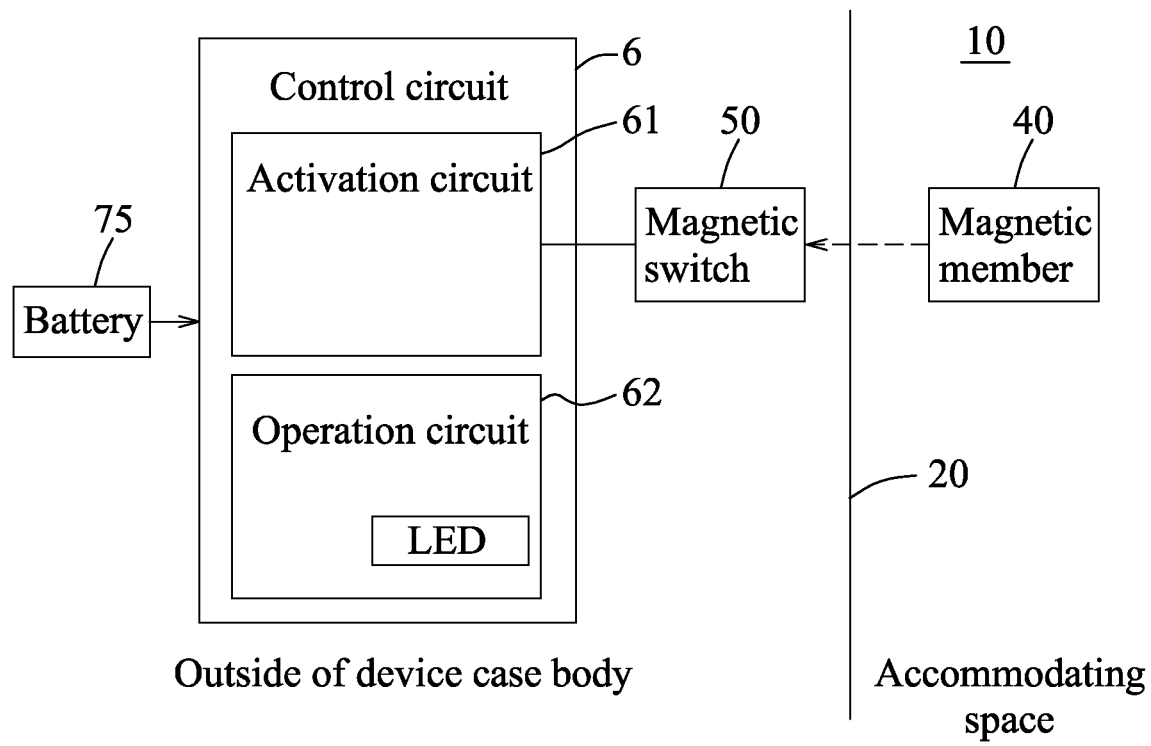
FIG. 1 is a schematic diagram illustrating an operational concept of an injection device according to one embodiment of the disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Furthermore, spatially relative terms, such as "on," "proximate," "outside," "inside," and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

An injection device may adopt a mechanical switch, such as a tactile switch or a miniature snap-action switch, to implement position detection of a movable part, e.g., a plunger, in the injection device, so as to determine whether the movable part has arrived at a target position. In such design, the mechanical switch is disposed inside a case body of the injection device. When the movable part is moved to the target position, the movable part is in physical contact with an actuator nub of the mechanical switch and triggers the mechanical switch to send a signal to a control circuit. In this way, position detection may be realized in the injection device. However, since the mechanical switch is disposed inside the case body and includes a cable which transmits the signal to the control circuit that is disposed on the outside of the case body, the case body needs to be formed with a cable through hole for the cable to pass, increasing complexity of the structure of injection device. Moreover, since the actuator nub of the mechanical switch is disposed in an accommodating space defined by the case body for contact with the movable part which is movable in the accommodating space, the case body needs to be formed with an actuator through hole for the actuator snap to extend into the accommodating space. In this way, liquid drug originally contained in the accommodating space may flow through the actuator through hole into the inside of the case body, and may wet the mechanical switch disposed inside the case body, causing malfunction or failure of the mechanical switch. In addition, the liquid drug may further flow out of the case body via the cable through hole and wet the control circuit, affecting the function and normal operation of the injection device.

An injection device according to one embodiment of this disclosure includes a device case body having an accommodating space, a control circuit disposed on the outside of the device case body, a movable part disposed in the accommodating space of the device case body, a magnetic member disposed on the movable part, and a magnetic switch disposed on the outside of the device case body. The movable part carries a drug for injection, and is movable relative to the device case body between a start position and a target position. The magnetic member is movable along with the movable part, and produces a magnetic field. The magnetic switch is disposed proximate to the magnetic member when the movable part is moved to the target position, and is electrically connected to the control circuit. When the movable part is moved to the target position, the magnetic switch changes a status of a conductive path of the magnetic switch in response to presence of the magnetic field that is produced by the magnetic member disposed on the movable part. The control circuit changes a state of the injection device according to a change of the status of the conductive path of the magnetic switch.

In some embodiments, the injection device adopts the magnetic switch to detect presence of a magnetic field, so as to determine whether the movable part has arrived at the target position. Since the magnetic switch is not required to be in physical contact with the movable part, the magnetic switch may be disposed on the outside of the device case body, simplifying a structure of the injection device and minimizing the risk that the magnetic switch is affected by liquid, water vapor or other substances in the accommodating space.

Figure 2:
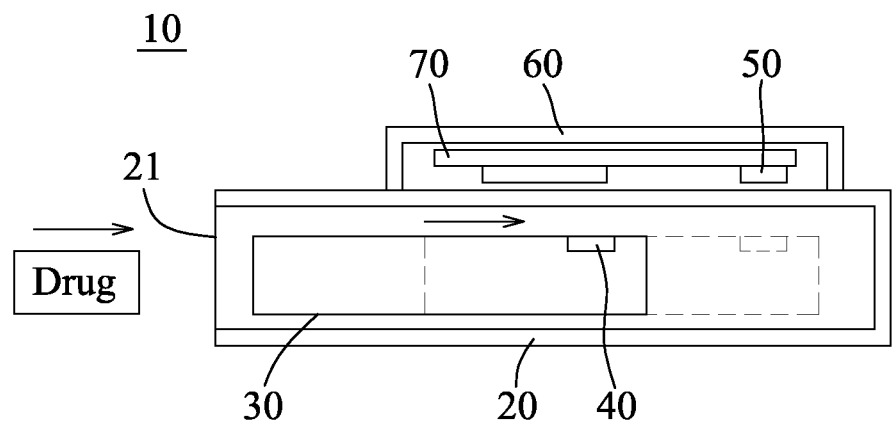
FIG. 2 is a schematic diagram illustrating a structural concept of the injection device shown in FIG. 1.

Referring to FIGS. 1 and 2, an injection device 10 according to one embodiment of this disclosure includes a device case body 20, a control circuit 6 that is disposed on the outside of the device case body 20, a movable part 30 that carries a drug for injection, a magnetic member 40 that is disposed on the movable part 30, and a magnetic switch 50 that is disposed on the outside of the device case body 20. The device case body 20 has an accommodating space, and the movable part 30 is disposed in the accommodating space and is movable relative to the device case body 20 between a start position and a target position. The magnetic member 40 is movable along with the movable part 30, and produces a magnetic field. The magnetic switch 50 is electrically connected to the control circuit 6, and detects presence of the magnetic field produced by the magnetic member 40 so as to determine whether the movable part 30 has arrived at the target position. In some embodiments, the magnetic member 40 is implemented by a permanent magnet.

Referring to FIG. 2, the device case body 20 is elongated, and includes a closed end and an open end 21 through which a container containing the drug for injection may be put into the injection device 10. The movable part 30 may be driven by manual operation or a mechanical force to move back and forth in the accommodating space of the device case body 20 between the start position (depicted by solid lines in FIG. 2) and the target position (depicted by broken lines in FIG. 2). In some embodiments, the target position is a ready-to-use position where the drug carried by the movable part 30 is ready to be injected. In other embodiments, the target position may be a specific position where test and inspection are to be performed. The magnetic switch 50 is disposed proximate to the magnetic member 40 when the movable part 30 is moved to the target position.

Figure 3:
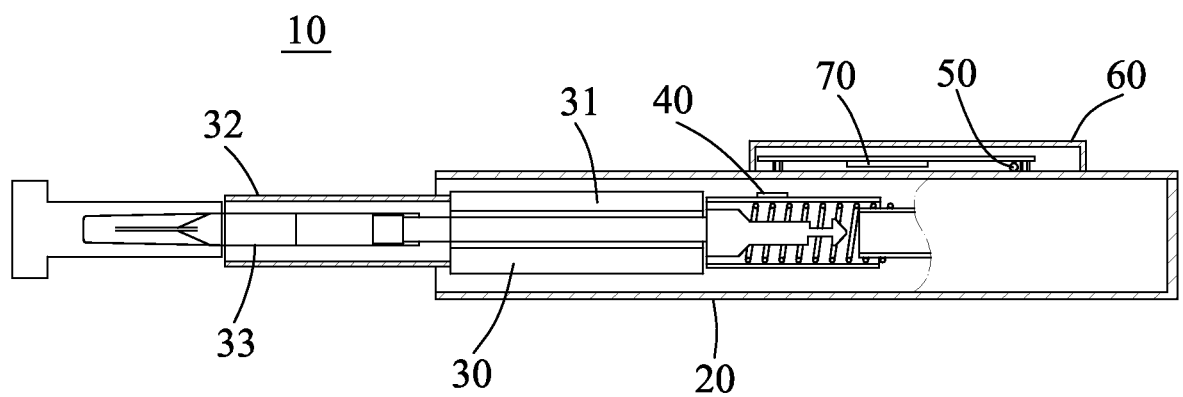
FIG. 3 is a schematic cross-sectional view illustrating an injection device according to one embodiment of the disclosure where a movable part is at a start position.
Figure 4:
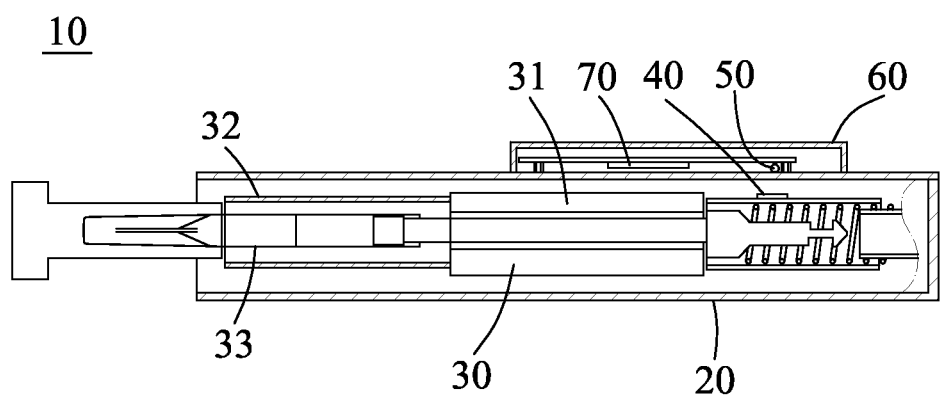
FIG. 4 is a schematic cross-sectional view illustrating the injection device shown in FIG. 3 where the movable part is moved to a target position.

Referring to FIGS. 3 and 4, a structure of the injection device 10 according to one embodiment of this disclosure is illustrated. The movable part 30 includes a plunger 31 and a cartridge holder 32. The cartridge holder 32 is used to carry a drug cartridge 33 that contains the drug for injection. In some embodiments, the cartridge holder 32 may be a syringe cartridge, and the drug cartridge 33 may be a prefilled syringe (PFS). In some embodiments, the magnetic member 40 is disposed on the plunger 31. However, in other embodiments, the magnetic member 40 may be disposed on the cartridge holder 32 or another section of the movable part 30 as long as the magnetic member 40 may be moved together with the movable part 30. Attributes of the magnetic member 40, such as, but not limited to, magnetism, an orientation and a position, are decided based on technical parameters of the magnetic switch 50. When the movable part 30 is at the target position, the magnetic field applied to the magnetic switch 50 has an intensity higher than a threshold at which the magnetic switch 50 may be switched on, and the magnetic switch 50 changes a status of a conductive path of the magnetic switch 50 in response to the presence of the magnetic field. When the movable part 30 is moved away from the magnetic switch 50, e.g., retracted to the start position, the magnetic field produced by the magnetic member 40 is not applied to the magnetic switch 50. In some embodiments, the magnetic member 40 is closer to the magnetic switch 50 when the movable part 30 is at the target positon than when the movable part 30 is at the start position.

Referring to FIG. 2, the injection device 10 further includes a circuit case body 60 and a circuit board 70. The circuit case body 60 is attached to the device case body 20, is located on the outside of the device case body 20, and has a receiving space. The circuit board 70 is disposed in the receiving space and holds the control circuit 6. The magnetic switch 50 is electrically connected to the circuit board 70 and is electrically connected to the control circuit 6 via the circuit board 70. In some embodiments, the magnetic switch 50 is disposed directly on the circuit board 70. In other embodiments, the magnetic switch 50 may be separated from the circuit board 70, and be electrically connected to the circuit board 70 via wired connection or wireless connection. In FIG. 2, the device case body 20 isolates the circuit board 70 and the accommodating space of the device case body 20 from each other, so that the control circuit 6 and the magnetic switch 50 may be isolated from the accommodating space of the device case body 20. In this way, liquid, water vapor or other substances contained in the accommodating space may be prevented by the device case body 20 from entering the receiving space of the circuit case body 60 and adversely affecting the circuit board 70 and electronic components in the receiving space. In some embodiments, since physical contact between the magnetic member 40 and the magnetic switch 50 is not required, a portion of the device case body 20 where the circuit case body 60 is attached to may have a completely closed structure to prevent substances from entering the receiving space of the circuit case body 60. In other embodiments, the magnetic switch 50 and/or the control circuit 6 may be embedded within walls of the device case body 20 by a manufacturing process of insert molding, and may be isolated from the accommodating space of the device case body 20, so as to prevent contact with liquid or other substances in the accommodating space.

In comparison with a mechanical switch, a magnetic switch has a relatively simpler structure, a smaller size, higher operational speed and longer lifespan. In comparison with an electronic switch, a magnetic switch has relatively stronger shock resistance and higher operation reliability. The principle of operation and the structure of a magnetic switch have been well known to a person skilled in the relevant art, and the magnetic switch 50 of the injection device 10 according to this disclosure may be implemented by the MISM-7 series reed switches provided by Littelfuse, Inc. Therefore, detailed descriptions related to the magnetic switch 50 are omitted herein for the sake of brevity. The magnetic switch 50 may be a normally-open reed switch or a normally-closed reed switch. By corresponding circuit design, the two types of reed switches can both realize the functions mentioned in this disclosure.

Referring to FIG. 1, in some embodiments, the control circuit 6 is powered by a battery 75, and includes an activation circuit 61 and an operation circuit 62. The activation circuit 61 is a circuit with low power consumption while the operation circuit 62 is a circuit with high power consumption. The magnetic switch 50 is connected to the activation circuit 61. Before the injection device 10 is put to use, for example, the movable part is at the start position, the injection device 10 is in a standby state where only the activation circuit 61 is in operation and the operation circuit 62 is on standby, so as to achieve a lower power consumption. When the movable part 30 is moved to the target position, the magnetic field produced by the magnetic member 40 causes the magnetic switch 50 to change the status of its conductive path, e.g., changing from disconnection to connection, or changing from connection to disconnection. The activation circuit 61 changes a state of the injection device 10 according to a change in the status of the conductive path of the magnetic switch 50. For example, the activation circuit 61 awakes the injection device 10 from the standby state to change the state of the injection device 10. Specifically, in some embodiments, the magnetic switch 50 changes the status of its conductive path to pass a signal to a controller (not shown) disposed on the circuit board 70, and the controller controls the activation circuit 61 to change the state of the injection device 10, i.e., to awake the injection device 10 from the standby state. In some embodiments, awakening the injection device 10 from the standby state includes activating the operation circuit 62 to perform a self-test of the injection device 10 and to supply power to relevant electronic components of the injection device 10. In some embodiments, the operation circuit 62 may include an indicator, such as a sound indicator or a visual indicator. In an example where the visual indicator is a light-emitting diode (LED) indicator, the LED indicator indicates the state of the injection device 10. When the operation circuit 62 is activated, the LED indicator is turned on to notify a user that the injection device 10 is awoken from the standby state.

It is noted that in some embodiments, the control circuit 6 may be a single circuit which does not include separate activation and operation circuits 61, 62. When detecting the change of the status of the conductive path of the magnetic switch 50, the control circuit 6 starts the self-test, and supplies power to other electronic components of the injection device 10. In other words, no matter how the control circuit 6 is implemented, the change of the state of the injection device 10 of this disclosure is triggered by the interaction between the magnetic member 40 and the magnetic switch 50.

Figure 5:
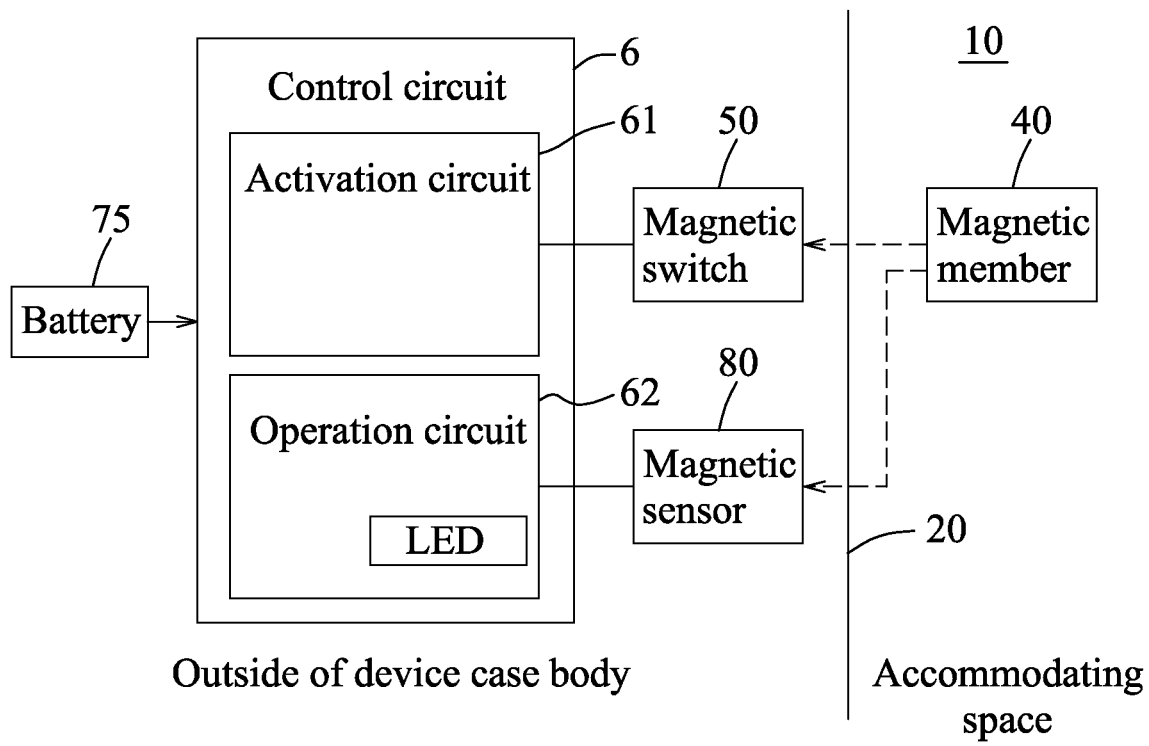
FIG. 5 is a schematic diagram illustrating an operational concept of an injection device according to another embodiment of the disclosure.
Figure 6:
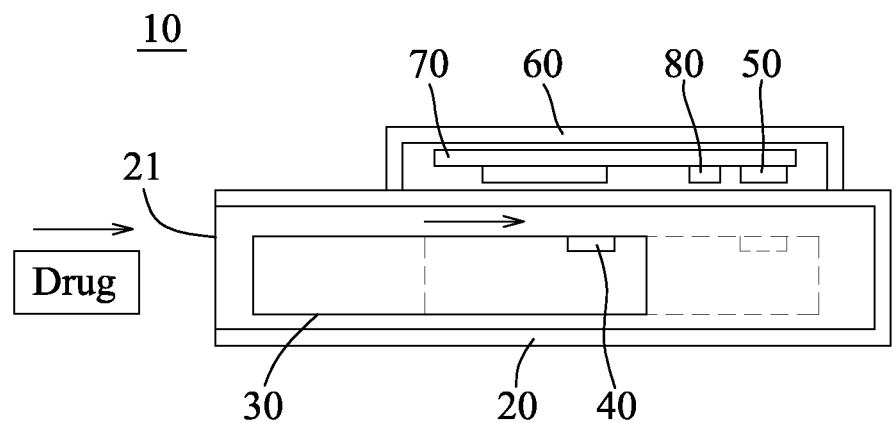
FIG. 6 is a schematic diagram illustrating a structural concept of the injection device shown in FIG. 5.

Referring to FIGS. 5 and 6, the injection device 10 according to one embodiment of this disclosure is similar to the injection device 10 shown in FIGS. 3 and 4, and further includes a magnetic sensor 80. The magnetic sensor 80 is disposed on the outside of the device case body 20, is spaced apart from the magnetic switch 50, and is electrically connected to the control circuit 6. When the movable part 30 is at the target position, the magnetic field produced by the magnetic member 40 is not only applied to the magnetic switch 50 but also applied to the magnetic sensor 80. The magnetic sensor 80 measures magnetic field intensity. The control circuit 6 determines, based on the magnetic field intensity measured by the magnetic sensor 80, whether a magnetic field which causes the magnetic switch 50 to change the status of its conductive path is the magnetic field produced by the magnetic member 40.

During use, the injection device 10 may be under the influence of an external magnetic field, such as a magnetic field produced by a nearby electronic device, other than the magnetic field produced by the magnetic member 40. When the external magnetic field exists and when an intensity of the external magnetic field is high enough to change the status of the conductive path of the magnetic switch 50, the external magnetic field might undesirably awake the injection device 10 from the standby state even if the movable part 30 is not moved to the target position. Therefore, according to the embodiment shown in FIGS. 5 and 6, the magnetic sensor 80 is introduced for determining a source of a magnetic field, so that a position of the movable part 30 and the state of the injection device 10 may be further verified based on the magnetic field intensity measured by the magnetic sensor 80.

In some embodiments, when the magnetic field intensity measured by the magnetic sensor 80 is within a predefined range, the control circuit 6 determines that the magnetic field which causes the magnetic switch 50 to change the status of its conductive path is the magnetic field produced by the magnetic member 40. The predefined range is set in advance based on an intensity of the magnetic field at either pole of the magnetic member 40. For example, the magnetic sensor 80 may measure an intensity of the magnetic field produced by the magnetic member 40 when the movable part 30 is at the target position under normal operating conditions, and this intensity may serve as a reference value for deciding the predefined range which is a range of plus and minus ten percent of the reference value. On the other hand, when the magnetic field intensity measured by the magnetic sensor 80 is beyond the predefined range, for example, twice the reference value, the control circuit 6 determines that the magnetic field which causes the magnetic switch 50 to change the status of its conductive path is an external magnetic field rather than the magnetic field produced by the magnetic member 40. In other embodiments, based on precision requirements of practical application, the predefined range may be flexibly adjusted, for example, to be plus and minus three, five or fifteen percent of the reference value.

It is noted that the magnetic field intensity expected to be measured by the magnetic sensor 80 when the movable part 30 is moved to the target position is not necessarily a fixed value. For example, in one implementation of the injection device, if a relative position of the magnetic sensor 80 to the target position of the movable 30 is somehow changed, the magnetic field intensity expected to be measured may also change. Moreover, if the magnetism of the magnetic member 40 changes, the magnetic field intensity expected to be measured may as well be changed.

Even though the magnetic sensor 80 is configured to measure the magnetic field intensity, the magnetic sensor 80 is not necessarily required to provide an exact value of the magnetic field intensity thus measured to the control circuit 6. For instance, in some embodiments, the magnetic sensor 80 may be a magnetic sensor chip which acts as a switch; when it is determined by the magnetic sensor chip that the magnetic field intensity thus measured falls in the predefined range, the magnetic sensor chip transmits a notice signal to the control circuit 6 for determination by the control circuit 6 that a source of the magnetic field is the magnetic member 40. In other embodiments, the magnetic sensor 80 may be a digital magnetic sensor or an analog magnetic sensor which transmits a digital signal or an analog signal that indicates the magnetic field intensity thus measured to the control circuit 6, to allow the control circuit 6 to determine a source of the magnetic field based on the digital signal or the analog signal.

Referring to FIG. 5, in some embodiments, the magnetic sensor 80 is electrically connected to the operation circuit 62. The activation circuit 61, according to the change in the status of the conductive path of the magnetic switch 50, awakes the injection device 10 from the standby state by activating the operation circuit 62. Accordingly, the magnetic sensor 80 is powered by the operation circuit 62, starts measuring an intensity of a magnetic field applied to the magnetic sensor 80, and provides the intensity thus measured to the operation circuit 62. When the magnetic field intensity measured by the magnetic sensor 80 is within the predefined range, the operation circuit 62 determines that the magnetic field which causes the magnetic switch 50 to change the status of its conductive path is the magnetic field produced by the magnetic member 40, and verifies that the movable part 30 has arrived at the target position. When the magnetic field intensity measured by the magnetic sensor 80 is beyond the predefined range, the operation circuit 62 determines that the magnetic field which causes the magnetic switch 50 to change the status of its conductive path is an external magnetic field rather than the magnetic field produced by the magnetic member 40, and thus shuts down accordingly.

Alternatively, in some embodiments, the magnetic sensor 80 may be directly and electrically connected to the activation circuit 61. In this arrangement, only when the magnetic switch 50 and the magnetic sensor 80 both meet their respective activation conditions (i.e., the status of the conductive path of the magnetic switch 50 is changed and the magnetic field intensity measured by the magnetic sensor 80 is within the predefined range) will the activation circuit 61 activate the operation circuit 62 to awake the injection device 10. This arrangement can also realize additional confirmation with respect to the position of the movable part 30 by using the magnetic sensor 80. In some embodiments as mentioned above where the control circuit 6 is a single circuit and does not include separate activation and operation circuits 61, 62, the magnetic sensor 80 may be directly and electrically connected to the control circuit 6.

Accordingly, it is evident that the magnetic sensor 80 may be utilized to confirm the source of the magnetic field, so that a position of the movable part 30 and the state of the injection device 10 may be further verified based on the magnetic field intensity measured by the magnetic sensor 80. A chance that the injection device 10 is undesirably awoken from the standby state by an external magnetic field can be reduced.

In some embodiments, the magnetic sensor 80 includes one of a magnetoresistive sensor, a Hall effect sensor and a combination thereof. Since the magnetoresistive sensor and the Hall effect sensor are existing products available on the market, detailed descriptions therefor are omitted herein for the sake of brevity. For example, the Hall effect sensor of the magnetic sensor 80 may be implemented by the AH180 Hall effect switch provided by Diodes Incorporated. Similar to the magnetic switch 50, the magnetic sensor 80 is directly disposed on the circuit board 70, or alternatively, the magnetic sensor 80 may be separated from the circuit board 70 and be electrically connected to the circuit board 70 via wired connection or wireless connection.

Figure 7:
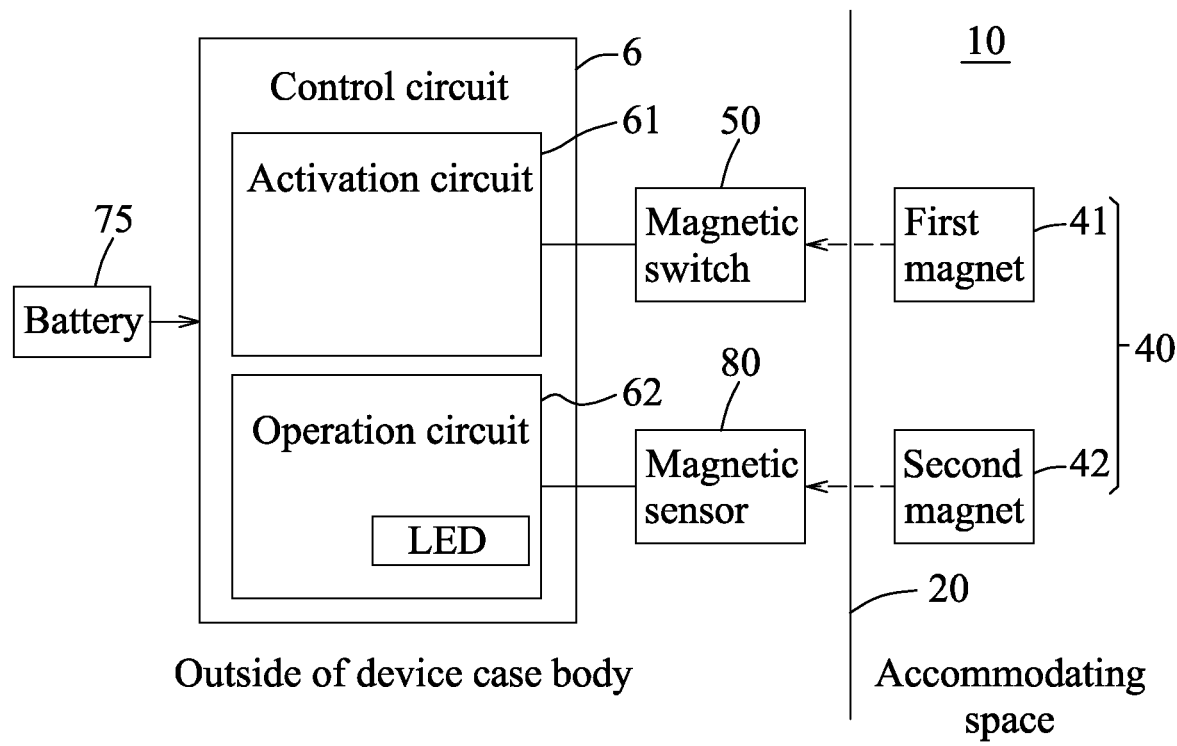
FIG. 7 is a schematic diagram illustrating an operational concept of an injection device according to still another embodiment of the disclosure.
Figure 8:
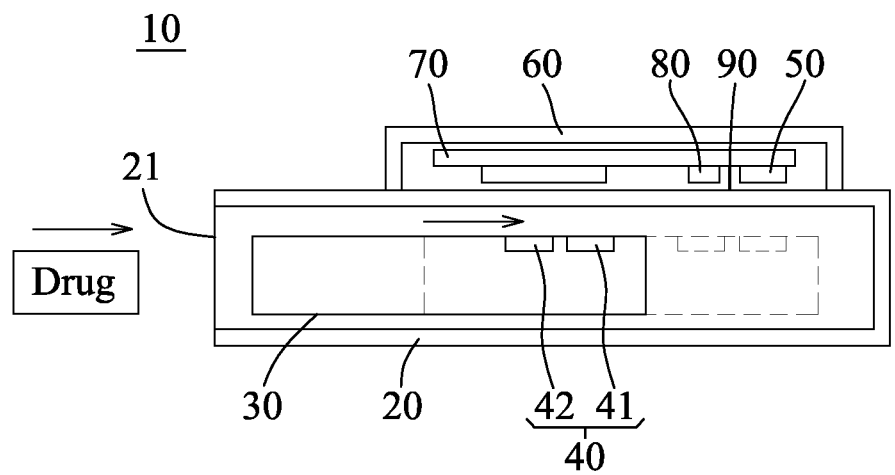
FIG. 8 is a schematic diagram illustrating a structural concept of the injection device shown in FIG. 7.

Referring to FIGS. 7 and 8, the injection device 10 according to one embodiment of this disclosure is similar to the injection device 10 shown in FIGS. 5 and 6, and a difference therebetween resides in that the magnetic member 40 includes a first magnet 41 and a second magnet 42 each of which may be implemented by a permanent magnet. The first magnet 41 produces a first magnetic field. The second magnet 42 is spaced apart from the first magnet 41 and produces a second magnetic field. When the movable part 30 is at the target position, the first magnetic field produced by the first magnet 41 is applied to the magnetic switch 50 without affecting the magnetic sensor 80, and the second magnetic field produced by the second magnet 42 is applied to the magnetic sensor 80. When the magnetic field intensity measured by the magnetic sensor 80 is within a preset range, the control circuit 6 determines that a magnetic field which causes the magnetic switch 50 to change the status of its conductive path is the first magnetic field produced by the first magnet 4. On the other hand, when the magnetic field intensity measured by the magnetic sensor 80 is beyond the preset range, the control circuit 6 determines that the magnetic field which causes the magnetic switch 50 to change the status of its conductive path is an external magnetic field rather than the first magnetic field produced by the first magnet 41. In some embodiments, the preset range is set in advance based on an intensity of the second magnetic field at either pole of the second magnet 42. Similar to how the predefined range is set as explained above, the magnetic sensor 80 may measure an intensity of a magnetic field (i.e., the second magnetic field produced by the second magnet 42) when the movable part 30 is moved to the target position under normal operating conditions, and this intensity thus measured may serve as a reference value for deciding the preset range which is a range of plus and minus a specific percent of the reference value.

In some embodiments, the first magnet 41 is disposed on the movable part 30, and the first magnet 41 is spaced apart from the magnetic sensor 80 by a predetermined distance when the movable part 30 is at the target position, such that the first magnetic field produced by the first magnet 41 does not affect the magnetic sensor 80. The predetermined distance may be decided first, with a suitable magnet being then selected based on the predetermined distance to serve as the first magnet 41. Alternatively, a magnet may be decided first to serve as the first magnet 41, with the predetermined distance being then found based on the magnetic field distribution of the first magnet 41 to make sure that the first magnetic field would not affect the magnetic sensor 80.

In some embodiments, referring to FIG. 8, the injection device 10 further includes a magnetic shielding barrier 90 that is disposed on the outside of the device case body 20, and that is disposed between the magnetic switch 50 and the magnetic sensor 80 so as to isolate the magnetic sensor 80 from the first magnetic field produced by the first magnet 41 when the movable part 30 is moved to the target position.

By the design that the magnetic member 40 includes the first magnet 41 and the second magnet 42, and that the magnetic sensor 80 would measure the second magnetic field produced by the second magnet 42 without being affected by the first magnetic field produced by the first magnet 41 when the movable part 30 is at the target position, a higher flexibility in terms of selection and configuration of the magnetic sensor 80 may be achieved. For example, attributes of the first magnet 41 can be given no consideration when configuring (e.g., selecting) the magnetic sensor 80, and a location of placement of the magnetic sensor 80 may be adjusted with higher flexibility.

It is noted that in the embodiment as shown in FIGS. 5 and 6, if the injection device 10 is under the influence of an external magnetic field which is similar to the first magnetic field produced by the first magnet 41, the external magnetic field would change the status of the conductive path of the magnetic switch 50, and the intensity of the external magnetic field measured by the magnetic sensor 80 might be within the predefined range. Under such circumstances, the operation circuit 62 would be erroneously activated, and would not determine that the magnetic field resulting in this activation is an external magnetic field so the operation circuit 62 could not shut down successfully. Therefore, the embodiment as shown in FIGS. 7 and 8 is proposed to tackle this issue. The first magnet 41 and the second magnet 42 are configured in such a manner that, when the movable part 30 is at the target position, the magnetic field intensity measured by the magnetic sensor 80 would be that of the second magnetic field produced by the second magnet 42, and the magnetic field intensity thus measured is lower by a substantial degree (for example, fifty percent or more) than an intensity of the first magnetic field that is capable of causing the magnetic switch 50 to change the status of its conductive path.

With such configurations of the first magnet 41 and the second magnet 42, the scenario that the operation circuit 62 is erroneously activated and does not shut down successfully because the operation circuit 62 fails to determine that the magnetic field resulting in this activation is an external magnetic field may be avoided. If the injection device 10 shown in FIGS. 7 and 8 is under the influence of an external magnetic field which is similar to the first magnetic field produced by the first magnet 41, the external magnetic field would change the status of the conductive path of the magnetic switch 50, and the magnetic field intensity measured by the magnetic sensor 80 would exceed the preset range because the preset range is substantially smaller than the intensity of the first magnetic field and the intensity of such external magnetic field as well. In this way, the control circuit 6 is able to determine that the magnetic field which causes the magnetic switch 50 to change the status of its conductive path is an external magnetic field rather than the first magnetic field produced by the first magnet 41, so it can be determined that the movable part 30 is not at the target position and the operation circuit 62 can shut down to save power.

It is noted that the magnetic field intensity measured by the magnetic sensor 80 being lower than the intensity of the first magnetic field that is capable of causing a change of a switch status does not necessarily mean that the intensity of the second magnetic field at either pole of the second magnet 42 is lower than the intensity of the first magnetic field at either pole of the first magnet 41. That is to say, besides magnetism of the first magnet 41 and the second magnet 42, the preset range may be at least related to relative positions of the magnetic sensor 80 and the second magnet 42. For example, the preset range is related to distances among the magnetic switch 50, the magnetic sensor 80, the first magnet 41 and the second magnet 42.

To sum up, the injection device 10 according to this disclosure at least has the following advantages.

1. In this disclosure, the magnetic switch 50 is used to replace a mechanical switch so that a structure of the injection device 10 can be improved because through holes for components of a mechanical switch to pass through may be omitted. In addition, the risk that the magnetic switch 50 is affected by liquid, water vapor or other substances may be minimized.
2. In some embodiments, the magnetic sensor 80 is introduced for determination of a source of a magnetic field, so that the position of the movable part 30 and the state of the injection device 10 may be further verified. The chances that the injection device 10 is erroneously awoken may be reduced.
3. In some embodiments, the magnetic member 40 includes the first magnet 41 and the second magnet 42, and the magnetic sensor 80 measures the second magnetic field produced by the second magnet 42 when the movable part 30 is at the target position, without being affected by the first magnetic field produced by the first magnet 41. A higher flexibility in terms of selection and configuration of the magnetic sensor 80 may be achieved.
4. By the specific configurations of the first magnet 41 and the second magnet 42, such as the intensity of the second magnetic field measured by the magnetic sensor 80 being lower by a substantial degree than the intensity of the first magnetic field that is capable of causing a change of switch state, a scenario that the injection device 10 is erroneously awoken by an external magnetic field similar to the first magnetic field may be further reduced.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. An injection device comprising:
    a device case body having an accommodating space;
    a control circuit disposed on an outside of the device case body;
    a movable part disposed in the accommodating space of the device case body, carrying a drug for injection, and movable relative to the device case body between a start position and a target position;
    a magnetic member disposed on the movable part, movable along with the movable part, and producing a magnetic field;
    a magnetic switch disposed on the outside of the device case body, disposed proximate to the magnetic member when the movable part is at the target position, and electrically connected to the control circuit; and
    a magnetic sensor that is disposed on the outside of the device case body, spaced apart from the magnetic switch, and electrically connected to the control circuit,
    wherein when the movable part is moved to the target position, the magnetic switch changes a status of a conductive path of the magnetic switch in response to presence of the magnetic field that is produced by the magnetic member disposed on the movable part, the control circuit changing a state of the injection device according to a change of the status of the conductive path of the magnetic switch, and
    wherein when the movable part is moved to the target position, the magnetic field produced by the magnetic member is applied to the magnetic sensor, the magnetic sensor measuring a magnetic field intensity, the control circuit determining, based on the magnetic field intensity measured by the magnetic sensor, whether a magnetic field which causes the magnetic switch to change the status of its conductive path is the magnetic field produced by the magnetic member.

2. The injection device as claimed in claim 1, further comprising:
    a circuit case body attached to the device case body, located on the outside of the device case body, and having a receiving space; and
    a circuit board disposed in the receiving space and holding the control circuit;
    wherein the magnetic switch is electrically connected to the circuit board and is electrically connected to the control circuit via the circuit board.

3. The injection device as claimed in claim 2, wherein the device case body isolates the circuit board and the accommodating space of the device case body from each other.

4. The injection device as claimed in claim 1, wherein the control circuit includes an activation circuit, the magnetic switch is connected to the activation circuit, and when the movable part is moved to the target position, the activation circuit of the control circuit awakes the injection device from a standby state to change the state of the injection device.

5. The injection device as claimed in claim 1, wherein the control circuit includes an activation circuit and an operation circuit, the magnetic switch being electrically connected to the activation circuit, the magnetic sensor being electrically connected to the operation circuit, the activation circuit, according to the change of the status of the conductive path of the magnetic switch, awaking the injection device from a standby state to change the state of the injection device by activating the operation circuit.

6. The injection device as claimed in claim 1, wherein when the magnetic field intensity measured by the magnetic sensor is within a predefined range, the control circuit determines that the magnetic field which causes the magnetic switch to change the status of its conductive path is the magnetic field produced by the magnetic member, the predefined range being set in advance based on an intensity of the magnetic field at either pole of the magnetic member.

7. The injection device as claimed in claim 6, wherein when the magnetic field intensity measured by the magnetic sensor is beyond the predefined range, the control circuit determines that the magnetic field which causes the magnetic switch to change the status of its conductive path is an external magnetic field rather than the magnetic field produced by the magnetic member.

8. The injection device as claimed in claim 1, wherein the magnetic sensor includes one of a magnetoresistive sensor, a Hall effect sensor and a combination thereof.

9. The injection device as claimed in claim 1,
    wherein the magnetic member includes a first magnet that produces a first magnetic field, and a second magnet that is spaced apart from the first magnet and that produces a second magnetic field, and
    wherein when the movable part is at the target position, the first magnetic field produced by the first magnet is applied to the magnetic switch without affecting the magnetic sensor, and the second magnetic field produced by the second magnet is applied to the magnetic sensor.

10. The injection device as claimed in claim 9, wherein the first magnet is disposed on the movable part, and the first magnet is spaced apart from the magnetic sensor by a predetermined distance when the movable part is at the target position such that the first magnetic field produced by the first magnet does not affect the magnetic sensor.

11. The injection device as claimed in claim 9, further comprising a magnetic shielding barrier that is disposed on the outside of the device case body, and that is disposed between the magnetic switch and the magnetic sensor so as to isolate the magnetic sensor from the first magnetic field produced by the first magnet when the movable part is at the target position.

12. The injection device as claimed in claim 9, wherein the first magnet and the second magnet are configured in such a manner that, when the movable part is at the target position, the magnetic field intensity measured by the magnetic sensor is that of the second magnetic field produced by the second magnet and is lower than an intensity of the first magnetic field that is capable of causing the magnetic switch to change the status of its conductive path.

13. The injection device as claimed in claim 12, wherein the intensity measured by the magnetic sensor is at least fifty percent lower than an intensity of the first magnetic field that is capable of causing the magnetic switch to change the status of its conductive path when the movable part is at the target position.

14. The injection device as claimed in claim 12, wherein
when the magnetic field intensity measured by the magnetic sensor is within a preset range, the control circuit determines that a magnetic field which causes the magnetic switch to change the status of its conductive path is the first magnetic field produced by the first magnet,
when the magnetic field intensity measured by the magnetic sensor is beyond the preset range, the control circuit determines that the magnetic field which causes the magnetic switch to change the status of its conductive path is an external magnetic field rather than the first magnetic field produced by the first magnet, and
the preset range is set in advance based on an intensity of the second magnetic field at either pole of the second magnet.

15. The injection device as claimed in claim 1, wherein the movable part includes a plunger, and the magnetic member is disposed on the plunger.

16. The injection device as claimed in claim 1, wherein the target position is a ready-to-use position where the drug carried by the movable part is ready to be injected.

17. An injection device comprising:
a device case body having an accommodating space;
a control circuit disposed on an outside of the device case body;
a movable part disposed in the accommodating space of the device case body, and movable along a longitudinal direction of the device case body between a start position and a target position;
a magnetic member disposed on the movable part, movable along with the movable part, and producing a magnetic field;
a magnetic switch disposed on the outside of the device case body, disposed proximate to the magnetic member when the movable part is moved to the target position, and electrically connected to the control circuit; and
a magnetic sensor disposed on the outside of the device case body, spaced apart from the magnetic switch, and electrically connected to the control circuit,
wherein the device case body isolates the control circuit and the magnetic switch from the accommodating space of the device case body;
wherein when the movable part is moved to the target position, the magnetic switch changes a status of a conductive path of the magnetic switch in response to presence of the magnetic field that is produced by the magnetic member disposed on the movable part, the control circuit changing a state of the injection device according to a change of the status of the conductive path of the magnetic switch, and
wherein when the movable part is moved to the target position, the magnetic field produced by the magnetic member is applied to the magnetic sensor, the magnetic sensor measuring a magnetic field intensity, the control circuit determining, based on the magnetic field intensity measured by the magnetic sensor, whether a magnetic field which causes the magnetic switch to change the status of its conductive path is the magnetic field produced by the magnetic member.

18. An injection device comprising:
a device case body having an accommodating space;
a control circuit disposed on an outside of the device case body;
a movable part disposed in the accommodating space of the device case body, and movable along a longitudinal direction of the device case body between a start position and a target position;
a magnetic member disposed on the movable part, movable along with the movable part, and producing a magnetic field;
a magnetic switch disposed on the outside of the device case body, disposed proximate to the magnetic member when the movable part is moved to the target position, and electrically connected to the control circuit; and
a magnetic sensor disposed on the outside of the device case body, spaced apart from the magnetic switch, and electrically connected to the control circuit,
wherein the device case body isolates the control circuit and the magnetic switch from the accommodating space of the device case body;
wherein when the movable part is moved to the target position, the magnetic switch changes a status of a conductive path of the magnetic switch in response to presence of the magnetic field that is produced by the magnetic member disposed on the movable part to pass a signal to the control circuit, the control circuit changing a state of the injection device according to the signal passed by the magnetic switch; and
wherein when the movable part is moved to the target position, the magnetic field produced by the magnetic member is applied to the magnetic sensor, the magnetic sensor measuring a magnetic field intensity, the control circuit determining, based on the magnetic field intensity measured by the magnetic sensor, whether a magnetic field which causes the magnetic switch to change the status of its conductive path is the magnetic field produced by the magnetic member.

* * * * *